US007387996B2

(12) United States Patent
Langkjaer

(10) Patent No.: US 7,387,996 B2
(45) Date of Patent: *Jun. 17, 2008

(54) FORMULATIONS OF INSULIN

(75) Inventor: Liselotte Langkjaer, Holte (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 11/193,200

(22) Filed: Jul. 29, 2005

(65) Prior Publication Data

US 2005/0261168 A1    Nov. 24, 2005

Related U.S. Application Data

(63) Continuation of application No. 10/429,508, filed on May 5, 2003, now abandoned.

(30) Foreign Application Priority Data

May 7, 2002  (DK) ............................... 2002 00683

(51) Int. Cl.
*A61K 38/28* (2006.01)
(52) U.S. Cl. ............................................. 514/3; 514/4
(58) Field of Classification Search ...................... None
See application file for complete search history.

(56) References Cited

U.S. PATENT DOCUMENTS 4,839,341 A    6/1989   Massey et al. ................. 514/4
5,922,675 A    7/1999   Baker et al. ................... 514/4
6,221,633 B1   4/2001   Ertl et al. ................... 435/69.4
6,589,229 B1   7/2003   Connelly et al. ......... 604/890.1
2001/0041786 A1 11/2001  Brader et al.
2003/0224973 A1 12/2003  Bayer et al. .................... 514/3

FOREIGN PATENT DOCUMENTS

| EP | 0700683 A1 | 3/1996 |
| EP | 0712861 A2 | 5/1996 |
| EP | 0712861 A3 | 3/1998 |
| EP | 0925792 A2 | 6/1999 |
| EP | 0925792 A3 | 9/2001 |
| EP | 1172114 A2 | 1/2002 |
| EP | 0712861 B1 | 4/2003 |
| WO | WO 96/29344 | 9/1996 |
| WO | WO 00/43034 A2 | 7/2000 |

OTHER PUBLICATIONS

Mohn et al., Diabetes, Nutrition & Metabolism, vol. 14, No. 6, pp. 349-357 (Dec. 2001).
Brange et al., Diabetes Care, vol. 13, No. 9, pp. 923-954 (1990).
Campbell et al., Clinical Therapeutics, vol. 23, No. 12, pp. 1938-1957, (2001).
Murphy et al., Diabetes Care, vol. 26, No. 3, pp. 799-804 (2003).
Raskin et al., Diabetes Care, vol. 23, No. 11, pp. 1666-1671 (2000).
Standl, E., Hormone Research, vol. 57, No. 1, pp. 40-45 (2002).
Vague et al., Diabetes Care, vol. 26, No. 3, pp. 590-596 (2003).
Hamilton-Wessler et al., Diabetologia, vol. 39, Suppl. 1, p. A24, abstract No. 88 (1996).

*Primary Examiner*—Jeffrey Edwin Russel
(74) *Attorney, Agent, or Firm*—Richard W. Bork

(57) ABSTRACT

Stable insulin formulations can be prepared by mixing a monomeric insulin and a soluble acylated insulin analog.

1 Claim, No Drawings

FORMULATIONS OF INSULIN

CROSS REFERENCE TO RELATED APPLICATIONS

This application is a continuation under 35 U.S.C 120 of U.S. application Ser. No. 10/429,508 filed on May 5, 2003 now abandoned and claims priority under 35 U.S.C. 119 of Danish application no. PA 2002 00683 filed on May 7, 2002, the contents of each of which are fully incorporated herein by reference.

FIELD OF THE INVENTION

This invention relates to a pharmaceutical formulation with improved physical stability being a mixture of a soluble acylated insulin analogue and a monomeric insulin or human insulin, preferably for use in an infusion system. Furthermore, this invention relates to the additional aspects mentioned in the claims below.

The object of this invention is to overcome or ameliorate at lest some of the disadvantages of the prior art. Hence, the more specific objects mentioned below are more or less fulfilled.

BACKGROUND OF THE INVENTION

Diabetes is a general term for disorders in man having excessive urine excretion as in diabetes mellitus and diabetes insipidus. Diabetes mellitus is a metabolic disorder in which the ability to utilize glucose is partly or completely lost. About 5% of all people suffer from diabetes.

Since the introduction of insulin in the 1920's, continuous strides have been made to improve the treatment of diabetes mellitus. To help avoid extreme glycemia levels, diabetic patients often practice multiple daily injection therapy, whereby monomeric insulin is administered with each meal and acylated or intermediate acting insulin is administered once or twice daily to cover the basal need.

In the treatment of diabetes mellitus, many varieties of insulin formulations have been suggested and used, such as regular insulin, isophane insulin (designated NPH), insulin zinc suspensions (such as Semilente®, Lente®, and Ultralente®), and biphasic isophane insulin. As diabetic patients are treated with insulin for several decades, there is a major need for safe and life quality improving insulin formulations. Some of the commercial available insulin formulations are characterized by a fast onset of action and other formulations have a relatively slow onset but show a more or less prolonged action. Fast-acting insulin formulations are usually solutions of insulin, while retarded acting insulin formulations can be suspensions containing insulin in crystalline and/or amorphous form precipitated by addition of zinc salts alone or by addition of protamine or by a combination of both. In addition, some patients are using formulations having both a fast onset of action and a more prolonged action. Such a formulation may be an insulin solution wherein protamine insulin crystals are suspended. Some patients do themselves prepare the final formulation by mixing an insulin solution with an insulin suspension formulation in the ratio desired by the patient in question.

Human insulin consists of two polypeptide chains, the so-called A and B chains which contain 21 and 30 amino acid residues, respectively. The A and B chains are interconnected by two cystine disulphide bridges. Insulin from most other species has a similar construction, but may not contain the same amino acid residues at the same positions.

The development of the process known as genetic engineering has made it possible to prepare a great variety of insulin compounds being analogous to human insulin. In these insulin analogues, one or more of the amino acids have been substituted with other amino acids which can be coded for by the nucleotide sequences.

Normally, insulin formulations are administered by subcutaneous injection. What is important for the patient, is the action profile of the insulin formulation which is the action of insulin on the glucose metabolism as a function of the time from the injection. In this profile, inter alia, the time for the onset, the maximum value, and the total duration of action are important. A variety of insulin formulations with different action profiles are desired and requested by the patients. One patient may, on the same day, use insulin formulations with very different action profiles. The action profile requested is, for example, depending on the time of the day and the amount and composition of any meal eaten by the patient.

Stable insulin formulations are particularly required for use in delivery devices that expose these agents to elevated temperatures and/or mechanical stress. For example, stable insulin formulations are required for use in continuous infusion systems and pen delivery devices.

There is a need for new ways of stabilizing since a stablizer, Genapol® (poloxamer 171), which for a long period of time has been used for stabilizing human insulin for pumps, may have some undesired effects (see *Diabetes Metab.* 26 (2000), 304-306).

In continuous infusion systems, a fluid containing an insulin formulation is pumped from a reservoir, usually to a subcutaneous, intravenous, or intraperitoneal depot. The reservoir, which must be exchanged or refilled periodically, is attached to the patient's body, or implanted into the patient's body. In either case, the patient's body heat and body motion, plus turbulence in the tubing and pump impart a relatively high amount of thermo-mechanical energy to the formulation. In the interest of minimizing the frequency with which the reservoir is filled, and of minimizing the size of the reservoir, formulations having a relatively high concentration of insulin are highly advantageous. It is desirable to have insulin formulations which are stable for at least one month under stressful in-use conditions.

Formulations of insulin for use in continuous infusion systems must remain soluble and substantially free of aggregation, even though subjected to the patient's body heat and motion for periods ranging from a few days to several months. Instability is promoted by the thermo-mechanical stress to which formulations are exposed in continuous infusion systems. Therefore, improvements in the physical stability of concentrated insulin formulations is urgently needed to permit them to be used successfully in continuous infusion systems.

It has become usual to use monomeric insulins in pumps. However, compared with human insulin, monomeric insulins have an increased tendency to form insoluble fibrils.

Among others, there are two major problems in connection with the use of insulin formulations in a continuous infusion system:

1. Due to fibrillation of the insulin component, the catheter may clog, and
2. There is a risk of fast development of ketoacidosis which may be fatal. Ketoacidosis may result from discontinuation of insulin delivery, for example due to fibrillation, pump failure, or the patient forgetting to reapply the pump after disconnection.

According to U.S. Pat. No. 4,476,118, pharmaceutical solutions of dissolved insulin having improved physical stability can be prepared by using ionized zinc salts. These solutions are particularly adapted for use in continuous insulin delivery equipment.

According to U.S. Pat. No. 4,472,385, pharmaceutical solutions of dissolved insulin having improved physical stability particularly adapted for use in continuous insulin delivery equipment can be by using a calcium or magnesium salt.

According to U.S. Pat. No. 4,614,730, insulin solutions may be stabilized by using a phospholipid.

According to U.S. Pat. No. 5,866,538, insulin formulations of superior chemical stability can be obtained in the presence of glycerol and/or mannitol and rather low halogenide concentrations.

SUMMARY OF THE INVENTION

One object of this invention is to furnish insulin formulations especially suited for use in an infusion system.

Another object of this invention is to furnish insulin formulations having superior long-term physical stability when exposed to high mechanical energy input.

Another object of this invention is to furnish insulin formulations having superior long-term physical stability when exposed to high temperature.

Another object of this invention is to furnish insulin formulations having superior long-term physical stability when exposed to high temperature and mechanical energy input.

Another object of this invention is to furnish insulin formulations having a low tendency of fibrillation.

Another object of this invention is to furnish insulin formulations having a convenient profile of action.

Another object of this invention is to furnish insulin formulations having both a fast onset of action and also a retarded action.

Another object of this invention is to furnish insulin formulations having no or only a minor amount of non-dissolved material.

DETAILED DESCRIPTION OF THE INVENTION

Definitions

The term "amino acid" as used herein, refers to amino acids which can be coded for by nucleotide sequences. Analogously, this applies to the term amino acid residue which is an amino acid from which hydroxy has been removed from a carboxyl group and/or hydrogen has been removed from an amino group. Similarly, a peptide and a peptide residue consists of amino acid residues.

The term "human insulin analogue" as used herein, refers to human insulin wherein one or more of the amino acid residues have been exchanged with another amino acid residue and/or from which one or more amino acid residue has been deleted and/or from which one or more amino acid residue has been added. These human insulin analogues have an anti-diabetic activity sufficiently high to be used to treat diabetic patients.

The term "acylated insulin analogue", when used herein, refers to human insulin or a human insulin analogue having one or more lipophilic substituents. The preferred lipophilic substituents are acyl groups. Examples of acylated insulin analogues are described in WO 95/07931 and WO 96/29344, more precisely in claim 1 thereof. These publications are hereby incorporated by reference. An example of a specific acylated insulin analogue is insulin detemir (i.e., $Lys^{B29}(N^{\epsilon}$-tetradecanoyl) des(B30) human insulin).

The term "monomeric insulin", when used herein, refers to human insulin analogs that are less prone to self-association (into dimers and hexamers) than human insulin. For more information, reference is made to Diabetes Care 13 (1990), 923-954, which is incorporated by reference. Examples of monomeric insulins are human insulin wherein Pro at position B28 is replaced by Asp, Lys, Leu, Val, or Ala; Lys at position B29 optionally is replaced by Pro; the amino acids at positions B28-B30 are deleted; or the amino acid at position B27 is deleted. A more detailed description of such monomeric compounds can be found in U.S. patent application Ser. No. 07/388,201 and European patent publication number 383,472 and 214,826 A2, all of which are hereby incorporated by reference. One skilled in the art would recognize that other modifications to the monomeric insulins are possible. Such modifications are widely accepted in the art and, compared with human insulin, they include replacement of Phe at position B1 with Asp; replacement of Thr at position B30 with Ala; replacement of Ser at position B9 with Asp; deletion of the amino acid at position B1; optionally, deletion of Thr at position B2; or deletion of the amino acid at position B30. Particularly preferred monomeric insulins are insulin lispro ($Lys^{B28}$, $Pro^{B29}$ human insulin) and insulin aspart ($Asp^{B28}$ human insulin). A further monomeric insulin is insulin glulisine ($Lys^{B3}$, $Glu^{B29}$ human insulin), vide Diabetologia 42, suppl. 1, page A178, abstract # 665.

Insulin means human insulin, human insulin analogs, monomeric insulin plus acylated insulin analogues.

The term "infusion system", when used herein, refers to a device for continuously administering a fluid to a patient parenterally for an extended period of time or for intermittently administering a fluid to a patient parenterally over an extended period of time without having to establish a new site of administration each time the fluid is administered. The fluid contains a compound having insulin activity. The device comprises a reservoir for storing the fluid before it is infused, a pump, a catheter, or other tubing for connecting the reservoir to the administration site via the pump, and control elements to regulate the pump. The device may be constructed for implantation, usually into the peritoneum. In such a case, the insulin reservoir will usually be adapted for percutaneous refilling. Obviously, when the device is implanted, the contents of the reservoir will be at body temperature, and subject to the patient's body motion.

The term "fibrillation", when used herein, refers to a physical process by which partially unfolded insulin molecules interact with each other to form insoluble linear aggregates. Under the influence of heat and exposure to hydrophobic surfaces, insulin undergoes conformational changes, resulting in successive, linear aggregation and formation of a viscous gel or insoluble precipitates. The degree of fibrillation can be determined as described in the stress test, below. A more detailed explanation is given in J. Pharm. Science. 86 (1997), 517-525, which is incorporated by reference.

The term "U", when used herein, refers to insulin units. Most of the currently used (marketed) insulins (bovine, porcine, human, lispro, aspart, and glargine) have a potency of one unit which equals 6 nmol. Long-acting acylated insulins have reduced potency compared to human insulin. Thus, for insulin detemir one unit corresponds to 24 nmol. For other insulins, the relation between U and nmol can be determined, if not known already, for example, by determining the amount giving a similar pharmacological (blood glucose lowering) effect as that of human insulin.

The content of zinc is expressed per hexamer insulin as a theoretical value, i.e., as the number of zinc atoms per 6 molecules of monomer insulin, independent on whether all hexamer insulin actually is present as hexamer insulin or not.

Stabilization of a formulation as used herein refers to a reduction in the formation of fibrils or other aggregates or maintenance of overall solubility and/or chemical integrity and corresponding maintenance of pharmacological efficacy. For example, a stable formulation according to the invention is one that can be stored at 4° C. without forming fibrils after at least about 10 days, preferably at least about 20 days, more preferably at least about 50 days, and, most preferably, at least about 100 days; or that can be stored at 25° C. without forming fibrils after at least about 2 days, preferably at least about 5 days, more preferably at least about 10 days, most preferably at least about 25 days.

DESCRIPTION OF THE INVENTION

This invention relates to mixtures of a soluble acylated insulin analog and a monomeric insulin or human insulin. It has, surprisingly, been found that such formulations have a substantially improved stability, for example, when exposed to physical stress. For example, the formulations of this invention have a low tendency to fibrillation. The formulations of this invention contain no or only a minor amount of non-dissolved material. Furthermore, said formulations give both a fast onset of action and also a retarded action. In addition to this, said formulations have convenient profiles of action.

The use of the formulation of this invention reduces the risk of ketoacidosis since, contrary to the usual insulin treatments via a pump, the patient gets an amount of a long-acting insulin, i.e., an acylated insulin.

In a broad aspect, this invention relates to a pharmaceutical soluble formulation comprising a soluble acylated insulin analogue and a monomeric insulin or human insulin wherein the lower limit of the molar ratio between the soluble acylated insulin analogue and the monomeric insulin or human insulin is 7:93, preferably 11:89, more preferred 14:86, and the upper limit of the molar ratio between the soluble acylated insulin analogue and the monomeric insulin or human insulin is 57:43, preferably 41:59, more preferred 31:69, preferably 24:76 and even more preferred 20:80.

In a preferred embodiment of this invention, the pharmaceutical soluble formulation according to this invention comprises a soluble acylated insulin analogue and a monomeric insulin or human insulin wherein the ratio between the soluble acylated insulin analogue and the monomeric insulin or human insulin is in the range from about 7:93 to about 57:43 on a mole to mole basis (corresponding to a content of 7-57% on a mole to mole basis). Since the skilled art worker, especially physicians, are more familiar with U (units) than moles, it can be added that if the soluble acylated insulin analogue and the monomeric insulin or human insulin have the same strength, the content of the soluble acylated insulin analogue will be 7-57% on a unit to unit basis. If, however, the strength of the soluble acylated insulin analogue is only, say, 25% of the strength of the monomeric insulin or human insulin, then the pharmaceutical soluble formulation according to this invention comprises a soluble acylated insulin analogue and human insulin or a monomeric insulin wherein the ratio between the soluble acylated insulin analogue and the monomeric insulin or human insulin is in the range from about 2:98 to about 25:75, on a unit to unit basis, preferably in the range from about 3:97 to about 15:85, on a unit to unit basis, more preferred in the range from about 4:96 to about 10:90, on a unit to unit basis.

According to one embodiment, the present invention does not cover a pharmaceutical soluble formulation comprising insulin aspart and insulin detemir wherein the ratio between insulin aspart and insulin detemir is in the range from 15:85 to 85:15, on a unit to unit basis, corresponding to the ratio between detemir and aspart being not more than about 41:59 on a mole to mole basis, vide our Danish patent application No. PA 2002 00684 the content of which is hereby incorporated by reference.

According to another embodiment, the present invention relates to a pharmaceutical soluble formulation comprising a soluble acylated insulin analogue and a monomeric insulin or human insulin wherein the molar ratio between the soluble acylated insulin analogue and the monomeric insulin or human insulin is in the range from about 11:89 to about 41:59, preferably in the range from about 14:86 to about 31:69.

In some embodiments, the formulations of the present invention exhibit a stability that is enhanced relatively to formulations of monomeric insulin or human insulin alone, i.e, without the soluble acylated insulin component. For example, the stability may be enhanced 2-fold, preferably 3-fold, more preferably 5-fold, even more preferably 10-fold or most preferably more than 10-fold.

In assessing the stability under stressful conditions, fibril formation can be measured visually, by conventional spectroscopic means, or by, e.g.thioflavin T fluorescence spectroscopy (Nielsen et al.: *Biochemistry* 40 (2001) p. 8397-8409).

For example, a formulation according to the invention that exhibits a 2-fold enhanced stability relative to a reference formulation is a formulation that, e.g., must be stored twice as long as the reference formulation before fibril formation can be detected.

In a preferred embodiment of this invention, the formulation is suitable for use in a continuous infusion pump. Hence, in one aspect, the present invention relates to a reservoir in a continuous infusion system comprising a soluble acylated insulin analogue as mentioned herein. In another aspect, this invention relates to a reservoir containing a pharmaceutical soluble formulation comprising a soluble acylated insulin analogue and a monomeric insulin or human insulin wherein the lower limit of the molar ratio between the soluble acylated insulin analogue and the monomeric insulin or human insulin is 7:93, preferably 11:89, more preferred 14:86, and the upper limit of the molar ratio between the soluble acylated insulin analogue and the monomeric insulin or human insulin is 57:43, preferably 41:59, more preferred 31:69, preferably 24:76 and even more preferred 20:80.

The pharmaceutical formulation of this invention may be prepared using the conventional techniques of the pharmaceutical industry which involves dissolving and mixing the pertinent ingredients as appropriate to give the desired end product.

Hence, using a soluble acylated insulin analogue in an amount from about 1% to about 15% of the total activity of the insulin calculated in insulin units, it is possible to prepare a medicament having improved physical stability in an aqueous solution containing a monomeric insulin or human insulin.

Thus, according to one procedure, on one hand, a soluble acylated insulin analogue and, on the other hand, a monomeric insulin or human insulin is dissolved in an amount of water, the total volume of which is somewhat less than the final volume of the formulation to be prepared. An isotonic agent, a preservative and a buffer is added as required and the pH value of the solution is adjusted—if necessary—using an acid, for example, hydrochloric acid, or a base, for example, aqueous sodium hydroxide as needed. Finally, the volume of the solution is adjusted with water to give the desired concentration of the ingredients.

In a preferred embodiment of this invention, the soluble acylated insulin analogue is insulin detemir ($Lys^{B29}(N^\epsilon$-tetradecanoyl) des(B30) human insulin). In a further preferred embodiment of this invention, the acylated insulin is $Lys^{B29}(N^\epsilon$-hexadecanoyl) des(B30) human insulin; $Lys^{B29}$ ($N^\epsilon$-tetradecanoyl) human insulin; $Lys^{B29}(N^\epsilon$-hexadecanoyl) human insulin; $Lys^{B28}(N^\epsilon$-tetradecanoyl) $Lys^{B28}$ $Pro^{B29}$ human insulin; $Lys^{B28}(N^\epsilon$-hexadecanoyl) $Lys^{B28}Pro^{B29}$ human insulin; $Lys^{B30}(N^\epsilon$-tetradecanoyl) $Thr^{B29}Lys^{B30}$ human insulin; $Lys^{B30}(N^\epsilon$-hexadecanoyl) $Thr^{B29}Lys^{B30}$ human insulin; $Lys^{B29}(N^\epsilon$-(N-hexadecanoyl-$\gamma$-glutamyl)) des(B30) human insulin; $Lys^{B29}(N^\epsilon$-(N-lithocholyl-$\gamma$-glutamyl)) des(B30) human insulin; $Lys^{B29}(N^\epsilon$-($\omega$-carboxyheptadecanoyl)) des(B30) human insulin; or $Lys^{B29}$ ($N^\epsilon$-($\omega$-carboxyheptadecanoyl)) human insulin.

In a preferred embodiment of this invention, human insulin is used. In another preferred embodiment of this invention, the monomeric insulin is insulin aspart. In a further preferred embodiment, the monomeric insulin is insulin lispro. In a still further preferred embodiment, the monomeric insulin is $Lys^{B3}$, $Glu^{B29}$ human insulin.

In a further preferred embodiment of this invention, the release of insulin activity from the formulation of this invention, after parenteral administration thereof to a human being within the first 4 hours, is at least about 50%.

In a preferred embodiment of this invention, the formulation contains an agent rendering the solution isotonic, an antimicrobial preservative, a pH-buffering agent, and a suitable zinc salt. In a preferred embodiment, the formulation has a pH value in the range from about 7 to about 8.

In a preferred embodiment of this invention, the formulation has a total amount of the insulin in the range with the lower limit being 10 U/ml, preferably 40 U/ml, more preferred 100 U/ml, and even more preferred 150 U/ml, and the upper limit being 1500 U/ml, preferably 1000 U/ml, more preferred 500 U/ml.

In another preferred embodiment of this invention, the formulation has a total amount of the insulin in the range from about 10 U/ml to about 1500 U/ml, preferably in the range from about 40 U/ml to about 1000 U/ml, more preferred in the range from about 100 U/ml to about 500 U/ml, for example, 100, 200, 400, or 500 U/ml.

In a preferred embodiment of this invention, the preservative is phenol, m-cresol or a mixture of phenol and m-cresol. In a further preferred embodiment of this invention, the total concentration of phenol and/or m-cresol is in the range from about 20 mM to about 50 mM, preferably in the range from about 30 mM to about 45 mM. The concentration of phenol and/or m-cresol is, inter alia, depending on the concentration of insulin.

In a preferred embodiment of this invention, the formulation has a content of zinc ions at the disposal of insulin in proportions in the range from about 2.3 to about 4.5 $Zn^{2+}$ per hexamer insulin (corresponding to from about 0.38 to about 0.75 $Zn^{2+}$/monomer insulin). The zinc salt used for preparing the formulations of this invention may, for example, be zinc chloride, zinc oxide or zinc acetate.

In a preferred embodiment of this invention, the isotonic agent is glycerol, mannitol, sorbitol or a mixture thereof at a concentration in the range from about 100 to 250 mM.

In another preferred embodiment of this invention, the formulation contains halogenide ions, preferably as sodium chloride, in an amount corresponding to from about 1 mM to about 100 mM, preferably from about 5 mM to about 40 mM.

In a preferred embodiment of this invention, the pH buffer is sodium phosphate, TRIS (trometamol), N-glycylglycine or L-arginine. Preferably, the pH buffer is a physiologically acceptable buffer in a concentration in the range from about 3 mM to about 20 mM, preferably from about 5 mM to about 15 mM. In a preferred embodiment of this invention, the formulations of this invention have a pH value is in the range from about 7.0 to about 8.0.

In a preferred embodiment of this invention, the formulation is a neutral, aqueous soluble formulation containing a combination of insulin aspart and insulin detemir in a concentration suitable for infusion systems and, furthermore, essentially consisting of phenolic preservatives (in a total concentration in the range from about 30 mM to about 40 mM), glycerol as isotonicity agent (in a concentration of about 0.17 M), dibasic sodium phosphate (in a concentration in the range from about 5 mM to about 7 mM), zinc ions corresponding to from about 2.5 to about 3.5 $Zn^{2+}$/hexamer insulin or from about 0.4 to about 0.6 $Zn^{2+}$/monomer insulin.

In a preferred embodiment of this invention, the formulation of this invention has a content of non-dissolved material below about 0.1%, preferably below 0.01% (weight per weight).

In a preferred embodiment of this invention, the stability factor, when determined by the test described in example 1 above, of the formulation of this invention is above about 2.5, preferably above about 4.

In a preferred embodiment of this invention, a soluble acylated insulin analogue is used in an amount in the range with the lower limit of the molar ratio between the soluble acylated insulin analogue and the monomeric insulin or human insulin being 7%, preferably 11%, more preferred 14%, and the upper limit of the molar ratio between the soluble acylated insulin analogue and the monomeric insulin or human insulin being 57%, preferably 41%, more preferred 31%, preferably 24% and even more preferred 20%, of the total amount of insulin to improve the physical stability in an aqueous solution containing a monomeric insulin or human insulin.

Administration of the formulations of this invention may be via any route known to be effective by the physician of ordinary skill. Parenteral and preferably subcutaneous and intraperitoneal administration is preferred.

The amount of the formulation of this invention that is administered to treat diabetes depends on a number of factors, among which are included the patient's sex, weight, physical activity, and age, diet of the patient, the underlying causes of the condition or disease to be treated, the route of administration and bioavailability, the persistence of the administered insulin or insulin analogues in the body, the specific formulation used, the potency of the insulin or insulin analogue used, a possible combination with other drugs, the severity of the case of diabetes, and the interval between dosages, if any interval. It is within the skill of the ordinary physician to titrate the dose and infusion rate and frequency of administration of the formulation of this invention to achieve the desired result. It is recommended that the daily dosage of the insulin components used in the formulations of this invention be determined for each individual patient by those skilled in the art in a similar way as for known insulin compositions.

The mentioning herein of references is no admission that they constitute prior art.

Herein, the word "comprise" is to be interpreted broadly meaning "include", "contain" or "comprehend" (vide, for example, EPO guidelines C 4.13).

This invention is further illustrated by the following examples which, however, are not to be construed as limiting the scope of protection. The features disclosed in the foregoing description and in the following examples may, both separately and in any combination thereof, be material for realizing this invention in diverse forms thereof.

Stress Test

The insulin solutions prepared as described below were subjected to a physical stress test.

Five samples of each insulin formulation were filled into Penfill® 1.5 ml cartridges. After introduction of 100 µL air into each cartridge using a Hamilton® syringe, the samples were subjected to the following physical stress test:

The cartridges were fixed to a rotator placed in an incubator kept at a constant temperature of 37° C.±2° C. and rotated 360° at a frequency of 30 rpm (rotations per minute) for four hours per day. The cartridges were stored at a constant temperature of 37° C.±2° C. between the rotation periods.

The opalescence of the cartridges was evaluated by visual inspection at regular time intervals—once daily in the first week and thereafter three times a week for up to 31 days. When opalescence or precipitates occurs and is visible with the naked eye, the sample is considered fibrillated. The number of days without fibrillation is defined as the Fibrillation time. The Stability Factor of a sample is calculated by dividing the Fibrillation time of said sample with the Fibrillation time of a specified reference sample tested in the same experiment.

The specified reference sample was insulin aspart 200 U/ml which was prepared as follows:

A solution with the following composition was prepared: Insulin aspart 200 U/ml (1200 nmol/ml), phenol 1.80 mg/ml (19 mM), m-cresol 2.06 mg/ml (19 mM), glycerol 16 mg/ml (174 mM), dibasic sodium phosphate dihydrate 1.25 mg/ml (7 mM), sodium chloride 0.58 mg/ml (10 mM), zinc chloride up to a total concentration of 39.2 µg $Zn^{2+}$/ml (3.0 $Zn^{2+}$ per hexamer). Hydrochloric acid and sodium hydroxide were used for dissolution of the insulin and adjustment of the pH value to 7.40. Finally, the solution was sterilized by filtration and filled into sterile Penfill® cartridges 1.5 ml using aseptic technique.

Test results

| | Fibrillation time (days) mean ± s.d. (n = 5) | Stability Factor |
|---|---|---|
| Example 1 aspart/detemir 98/2 | 14 ± 12 | 3 |
| Example 2 aspart/detemir 95/5 | >31 | >6 |

-continued

| | Fibrillation time (days) mean ± s.d. (n = 5) | Stability Factor |
|---|---|---|
| Example 3 aspart/detemir 90/10 | >31 | >6 |
| Example 4 aspart/detemir 75/25 | >31 | >6 |
| Reference aspart 100% | 5 ± 3 | 1 |

"s.d." is the standard deviation. As mentioned in the examples below, for example, the figures 75/25 appearing after "aspart/detemir" in this table indicates that the ratio between aspart and detemir is 75:25 based upon insulin units.

Similar results as those stated in the above table were obtained with corresponding formulations containing either 2.7 $Zn^{2+}$/hexamer and a pH value of 7.60 or 3.0 $Zn^{2+}$/hexamer and a pH value of 7.60.

As appears from the above test results, the stability of aspart against fibrillation is improved by adding detemir.

EXAMPLE 1

200 U Insulin per ml Containing 98% (U/U) Insulin Aspart and 2% (U/U) Insulin Detemir. Molar Ratio Aspart/detemir: 1:12.25 Corresponding to 7.55 mol-%.

A solution with the following composition was prepared: Insulin aspart 196 U/ml (1176 nmol/ml), Insulin detemir 4 U/ml (96 nmol)ml, phenol 1.80 mg/ml (19 mM), m-cresol 2.06 mg/ml (19 mM), glycerol 16 mg/ml (174 mM), dibasic sodium phosphate dihydrate 1.25 mg/ml (7 mM), sodium chloride 0.58 mg/ml (10 mM), zinc chloride and zinc acetate up to a total concentration of 41.5 µg $Zn^{2+}$/ml (3.0 $Zn^{2+}$/hexamer). Hydrochloric acid and sodium hydroxide were used for dissolution of the insulin and adjustment of the pH value to 7.40. Finally, the solution was sterilized by filtration and filled into sterile Penfill® cartridges 1.5 ml using aseptic technique.

EXAMPLE 2

200 U Insulin per ml Containing 95% (U/U) Insulin Aspart and 5% (U/U) Insulin Detemir Molar Ratio Aspart/detemir: 1:4.75 Corresponding to 17.4 mol-%.

A solution with the following composition was prepared: Insulin aspart 190 U/ml (1140 nmol/ml), Insulin detemir 10 U/ml (240 nmol/ml), phenol 1.80 mg/ml (19 mM), m-cresol 2.06 mg/ml (19 mM), glycerol 16 mg/ml (174 mM), dibasic sodium phosphate dihydrate 1.25 mg/ml (7 mM), sodium chloride 0.58 mg/ml (10 mM), zinc chloride and zinc acetate up to a total concentration of 45.1 µg $Zn^{2+}$/ml (3.0 $Zn^{2+}$/hexamer). Hydrochloric acid and sodium hydroxide were used for dissolution of the insulin and adjustment of the pH value to 7.40. Finally, the solution was sterilized by filtration and filled into sterile Penfill® cartridges 1.5 ml using aseptic technique.

EXAMPLE 3

200 U Insulin per ml Containing 90% (U/U) Insulin Aspart and 10% (U/U) Insulin Detemir. Molar Ratio Aspart/detemir: 1:2.25 Corresponding to 30.8 mol-%.

A solution with the following composition was prepared: Insulin aspart 180 U/ml (1080 nmol/ml), Insulin detemir 20 U/ml (480 nmol)ml, phenol 1.80 mg/ml (19 mM), m-cresol 2.06 mg/ml (19 mM), glycerol 16 mg/ml (174 mM), dibasic sodium phosphate dihydrate 1.25 mg/ml (7 mM), sodium chloride 0.58 mg/ml (10 mM), zinc chloride and zinc acetate up to a total concentration of 51.0 µg $Zn^{2+}$/ml (3.0 $Zn^{2+}$/hexamer). Hydrochloric acid and sodium hydroxide were used for dissolution of the insulin and adjustment of the pH value to 7.40. Finally, the solution was sterilized by filtration and filled into sterile Penfill® cartridges 1.5 ml using aseptic technique.

EXAMPLE 4

200 U Insulin per ml Containing 75% (U/U) Insulin Aspart and 25% (U/U) Insulin Detemir. Molar Ratio Aspart/detemir: 1:0.75 Corresponding to 57.1 mol-%.

A solution with the following composition was prepared: Insulin aspart 150 U/ml (900 nmol/ml), Insulin detemir 50 U/ml (1200 nmol)ml, phenol 1.80 mg/ml (19 mM), m-cresol 2.06 mg/ml (19 mM), glycerol 16 mg/ml (174 mM), dibasic sodium phosphate dihydrate 1.25 mg/ml (7 mM), sodium chloride 0.58 mg/ml (10 mM), zinc chloride and zinc acetate up to a total concentration of 68.6 µg $Zn^{2+}$/ml (3.0 $Zn^{2+}$/hexamer). Hydrochloric acid and sodium hydroxide were used for dissolution of the insulin and adjustment of the pH value to 7.40. Finally, the solution was sterilized by filtration and filled into sterile Penfill® cartridges 1.5 ml using aseptic technique.

EXAMPLE 5

100 U Insulin per ml Containing 95% (U/U) Insulin Aspart and 5% (U/U) Insulin Detemir.

A solution with the following composition was prepared: Insulin aspart 95 U/ml (570 nmol/ml), Insulin detemir 5 U/ml (120 nmol/ml), phenol 1.5 mg/ml (16 mM), m-cresol 1.7 mg/ml (16 mM), glycerol 16 mg/ml (174 mM), dibasic sodium phosphate dihydrate 0.9 mg/ml (5 mM), sodium chloride 0.58 mg/ml (10 mM), zinc chloride and zinc acetate up to a total concentration of 22.6 µg $Zn^{2+}$/ml (3.0 $Zn^{2+}$/hexamer). Hydrochloric acid and sodium hydroxide were used for dissolution of the insulin and adjustment of the pH value to 7.40. Finally, the solution was sterilized by filtration and filled into sterile Penfill® cartridges 3 ml using aseptic technique.

EXAMPLE 6

100 U Insulin per ml Containing 90% (U/U) Insulin Aspart and 10% (UIU) Insulin Detemir.

A solution with the following composition was prepared: Insulin aspart 90 U/ml (540 nmol/ml), Insulin detemir 10 U/ml (240 nmol/ml), phenol 1.5 mg/ml (16 mM), m-cresol 1.7 mg/ml (16 mM), glycerol 16 mg/ml (174 mM), dibasic sodium phosphate dihydrate 0.9 mg/ml (5 mM), sodium chloride 0.58 mg/ml (10 mM), zinc chloride and zinc acetate up to a total concentration of 25.5 µg $Zn^{2+}$/ml (3.0 $Zn^{2+}$/hexamer). Hydrochloric acid and sodium hydroxide were used for dissolution of the insulin and adjustment of the pH value to 7.40. Finally, the solution was sterilized by filtration and filled into sterile Penfill® cartridges 3 ml using aseptic technique.

EXAMPLE 7

400 U Insulin per ml Containing 95% (U/U) Insulin Aspart and 5% (U/U) Insulin Detemir.

A solution with the following composition was prepared: Insulin aspart 380 U/ml (2280 nmol/ml), Insulin detemir 20 U/ml (480 nmol/ml), phenol 1.8 mg/ml (19 mM), m-cresol 2.1 mg/ml (19 mM), glycerol 16 mg/ml (174 mM), dibasic sodium phosphate dihydrate 0.9 mg/ml (5 mM), sodium chloride 1.2 mg/ml (20 mM), zinc chloride and zinc acetate up to a total concentration of 90 µg $Zn^{2+}$/ml (3.0 $Zn^{2+}$/hexamer). Hydrochloric acid and sodium hydroxide were used for dissolution of the insulin and adjustment of the pH value to 7.40. Finally, the solution was sterilized by filtration and filled into sterile Penfill® cartridges 1.5 ml using aseptic technique.

The invention claimed is:

1. A pharmaceutical soluble formulation suitable for continuous infusion systems comprising: (i) insulin aspart; (ii) insulin detemir; (iii) a phenolic preservative at a concentration of about 30 mM to about 40 mM; (iv) glycerol in a concentration of about 0.17 M; (v) a pH buffer at concentration of about 5 mM to about 7 mM; and (vi) zinc ions in an amount corresponding to about 2.5 to about 3.5 $Zn^{2+}$/hexamer insulin, wherein the lower limit of the molar ratio between the insulin detemir and the insulin aspart is 7:93 and the upper limit of the molar ratio between the insulin detemir and the insulin aspart is 57:43.

* * * * *